United States Patent [19]

Deckner

[11] Patent Number: 4,597,963

[45] Date of Patent: Jul. 1, 1986

[54] MOISTURE-RESISTANT SKIN TREATMENT COMPOSITIONS

[75] Inventor: George E. Deckner, Westfield, N.J.

[73] Assignee: Charles of the Ritz Group Ltd., New York, N.Y.

[21] Appl. No.: 658,019

[22] Filed: Oct. 5, 1984

[51] Int. Cl.⁴ .......................... A61K 7/42; A61K 7/44
[52] U.S. Cl. ..................................... 424/59; 424/60; 514/847
[58] Field of Search ................... 424/59, 60; 526/312, 526/319

[56] References Cited

U.S. PATENT DOCUMENTS

| | | | |
|---|---|---|---|
| Re. 29,781 | 12/1978 | Papantoniou | 526/330 |
| 2,992,246 | 7/1961 | Frantz | 526/330 |
| 3,004,896 | 10/1961 | Heller et al. | 424/78 X |
| 3,073,794 | 1/1963 | Stoner | 424/78 X |
| 3,311,595 | 3/1967 | Kahrs et al. | 526/319 X |
| 3,423,381 | 1/1969 | Merijan et al. | 424/78 |
| 3,479,327 | 11/1969 | Merijan et al. | 424/78 X |
| 3,666,732 | 5/1972 | Skoultchi et al. | 424/60 |

FOREIGN PATENT DOCUMENTS

| | | | |
|---|---|---|---|
| 748582 | 10/1970 | Belgium | 424/70 |
| 571216 | 2/1959 | Canada | 424/60 |
| 2028131 | 3/1980 | United Kingdom | 424/59 |

*Primary Examiner*—Dale R. Ore
*Attorney, Agent, or Firm*—Lawrence S. Levinson; Burton Rodney

[57] ABSTRACT

Skin treatment compositions such as sun screen compositions and moisturizer compositions are provided which include a polyvinyl alkyl or alkenyl ester, such as polyvinyl stearate, to impart moisture resistance or substantivity to the compositions.

18 Claims, No Drawings

MOISTURE-RESISTANT SKIN TREATMENT COMPOSITIONS

FIELD OF THE INVENTION

The present invention relates to skin treatment compositions, such as sun screen compositions and moisturizer compositions, which have improved substantivity.

BACKGROUND OF THE INVENTION

The market place is now flooded with sun screen and sun block formulations. These products provide excellent protection against severe sun burning of exposed skin and contain chemicals which can absorb ultraviolet light and various wavelengths, such as 2-hydroxy-4-methoxybenzophenone, or an opaque substance that physically reflects or scatters ultraviolet light, such as zinc oxide or titanium dioxide. Most of these formulations offer protection from the sun for extended periods so long as they remain on exposed areas and are not washed off by bathing. Unfortunately, bathing in pool water and ocean water will usually result in most conventional sun screen and sun block formulations being washed away from the skin thereby leaving exposed areas of skin. Attempts have been made at formulating sun screen products which are moisture resistant. For example, see U.S. Pat. No. 3,666,732.

Accordingly, effective sun screen and sun block formulations which remain on the skin even after bathing, that is are water-resistant, for extended periods of time would indeed fulfill a long-felt want.

DESCRIPTION OF THE INVENTION

In accordance with the present invention, moisture resistant skin treatment compositions, such as sun screen and sun block formulations, and moisturizer formulations are provided, which compositions have improved moisture resistance and substantivity due to the presence therein of one or more polyvinyl alkyl or alkenyl esters and are preferably in the form of a oil-in-water emulsion which contains water, emollients, emulsifiers, thickeners, preservatives, coloring agents, fragrances, antioxidants and the like and one or more known ultraviolet absorbing compounds (in the case of sun screen or sun block formulations). In fact, the moisturizer compositions of the invention will be similar in composition to the sun screen or sun block formulations except for the presence or absence of the ultraviolet absorbing compound.

The formulation of the invention is preferably a oil-in-water type emulsion since this type of emulsion affords better cosmetic feel to the product. However, the product could also be formulated as a water-in-oil emulsion, cream base, or oil base. Depending upon the choice of ingredients, the formulation has a semi-solid cream-like consistency which can be packaged in a plastic squeeze tube or it has a lotion type consistency which can be packaged in a plastic squeeze container. The container can include a flow-type cap or pump-type dispenser.

The essence of the present invention resides in the use of one or more polyvinyl alkyl or alkenyl esters to enhance the moisture resistance of the particular composition involved. Thus, the composition of the invention, regardless of whether it is a sun screen, sun block, moisturizer, etc. will contain from about 0.5 to about 10% and preferably about 2 to about 7% by weight (based on the total weight of the formulation) of polyvinyl alkyl or alkenyl ester. Where amounts less than 0.5% by weight polyvinyl alkyl or alkenyl ester are employed, the moisture resistance imparted will be minimal and unacceptable, whereas, where amounts greater than 10% by weight are employed, increase in moisture resistance imparted will be minimal and unwarranted considering the expense of raw materials involved.

The polyvinyl alkyl or alkenyl ester will be of the structure

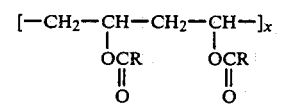

wherein R is an alkyl group or an alkenyl group containing one to three double bonds. The polyvinyl alkyl or alkenyl ester will contain 8 to 25 carbons, and preferably from about 12 to about 22 carbons in the alkyl or alkenyl ester portion. These esters are commercially available and may be prepared by conventional techniques.

Examples of polyvinyl alkyl or alkenyl esters suitable for use herein include but are not limited to polyvinyl stearate, polyvinyl caprylate, polyvinyl perlargonate, polyvinyl caprate, polyvinyl undecanoate, polyvinyl laurate, polyvinyl tridecanoate, polyvinyl myristate, polyvinyl pentadecanoate, polyvinyl palmitate, polyvinyl marganate, polyvinyl monodecanoate, polyvinyl archidate, polyvinyl heneicosanoate, polyvinyl behenate, polyvinyl tricosanoate, polyvinyl tetracosanoate, polyvinyl pentacosanoate, polyvinyl oleate, polyvinyl linoleate, polyvinyl ricinoleate, polyvinyl palmitoleate, polyvinyl vaccenoate, polyvinyl erucoate, polyvinyl licanoate, and the like. Preferred are polyvinyl stearate, polyvinyl myristate, polyvinyl palmitate and polyvinyl oleate.

Where the formulation is a sun screen or sun block formulation, it will contain one or more known ultraviolet absorbing agents, preferably at least one compound which absorbs in the UV-B region (wavelength 290 to 320 nanometers) and at least one compound which absorbs in the UV-A region (wavelength 320 to 400 nanometers). The total amount of UV absorbing agents included within the formulation will be form about 3% to about 15% by weight, which amount will determine whether it is a sun screen or sun block.

Suitably UV-A absorbing agents include 2-(2'-hydroxy-5'-methylphenyl)benzotriazole (Tinuvin P); 2-(2'-hydroxy-5'-t-octylphenyl)benzotriazole (Spectra-Sorb UV 5411); 2,4-dihydroxybenzophenone (Uvinul 400); 2-hydroxy-4-methoxybenzophenone (oxybenzone, Spectra-Sorb UV9, Uvinul M-40); 2,2', 4,4'-tetrahydroxybenzophenone (Uvinul D50); 2,2'-dihydroxy-4,4'-dimethoxybenzophenone (Uvinul D49); 2,2'-dihydroxy-4-methoxybenzophenone (dioxybenzone, Spectra-Sorb UV24); 2-ethylhexyl-4-phenyl-benzophenone carbonate (Eusolex 3573); 2-hydroxy-4-methoxy-4'-methylbenzophenone (mexenone, Uvistat 2211); 2-hydroxy-4-(n-octyloxy)benzophenone (octabenzone, Spectra-Sorb UV531); 4-phenylbenzophenone (Eusolex 3490); and 2-ethylhexyl-2-cyano-3,3'-diphenylacrylate (Uvinul N539). The UV-A absorbing agent or agents are present in the final product at from about 0.5% to about 10% by weight of the formulation. The amount will vary according to the particular agent selected and whether the formulation is intended to minimize or permit tanning.

The preferred UV-A absorbing agent is 2-hydroxy-4-methoxybenzophenone alone or in combination with 2,2'-dihydroxy-4-methoxybenzophenone.

Suitable UV-B absorbing agents include 4-(dimethylamino)benzoic acid, ethyl ester; 4-(dimethylamino)benzoic acid, 2-ethylhexyl ester (Escalol 507); 4-(dimethylamino)benzoic acid, pentyl ester (Escalol 506); glyceryl p-aminobenzoate (Escalol 106); isobutyl p-aminobenzoate (Cycloform); and isopropyl p-aminobenzoate. The UV-B absorbing agent or agents are present in the final product at from about 1% to about 15% by weight of the formulation. The amount will vary according to the particular agent selected and degree of protection desired in the final product. The preferred UV-B absorbing agent is 4-(dimethylamino)benzoic acid, 2-ethylhexyl ester.

The formulation also contains from about 50% to about 90% and preferably from about 60 to about 80% by weight of water, from about 1% to about 10% and preferably from about 1 to about 5% by weight of emollients, from about 1% to about 10% and preferably from about 1 to about 5% by weight of emulsifiers, from about 0.05 to about 2% and preferably from about 0.1 to about 1% by weight of preservatives and antioxidants, and less than about 1% by weight of fragrance and coloring agents.

Suitable emollients include mineral oil, avocado oil, squalane, octyl palmitate, cocoa butter, sesame oil, petrolatum, propylene glycol dicaprylate/dicaprate, isopropyl myristate, etc. The formulation will preferably contain a mixture of several of these emollients or others which are approved for cosmetic use.

Suitable emulsifiers include polyethylene glycol 20 sorbitan monolaurate (Polysorbate 20), diethanolamine cetyl phosphate, glyceryl stearate, polyethylene glycol 100 stearate, polyethylene glycol 20 stearyl ether (Brij 78, Steareth 20), polysorbate 88 (Tween 80), etc. The formulation will preferably contain a mixture of two or more of these emulsifiers or others which are approved for cosmetic use.

Suitable preservatives include imidazolidinyl urea (Germall 115), methylparaben (Tegosept M), quaternium-15 (N-(3-chloroallyl)hexaminium chloride, Dowcil 200), propylparaben (Tegosept P), dimethyldimethoyl hydantoin, benzyl alcohol and/or phenoxyethanol, etc., and the preferred antioxidant is a mixture of butylated hydroxyanisole, propylene glycol, propyl gallate and citric acid (Tenox 2). The formulation will preferably contain the antioxidant mixture and one or more of the preservatives or any other preservatives and antioxidants approved for cosmetic use.

As discussed above, by varying the percentage of ingredients the formulation can be obtained in a lotion or semi-solid form. For example, in formulation the product as a lotion, water would be included at from about 60% to 65% by weight of the final product and one or more humectants such as propylene glycol, glycerin, 1,3-butylene glycol, sorbitol, polyethylene glycols (for example, Carbowax 400), could be included at up to about 7.5% by weight of the final product.

The composition of the invention will optionally include a thickener in an amount within the range of from about 0.05 to about 1% and preferably from about 0.05 to about 0.3% by weight. A preferred thickener suitable for use herein is Carbopol 940 or Carbomer 940 which is hydrophilic acrylic polymer cross-linked with a polyfunctional agent and employed with an organic or inorganic base, preferably triethanolamine. Other examples of thickeners which may be employed herein include, but are not limited to, stearic acid, magnesium aluminum silicate, stearoxydimethicone, hydroxyethyl, cellulose, hydroxypropyl cellulose or xanthan gum.

Skin conditioning agents which may optionally be present in the composition of the invention include allantoin, d- or dl-panthenol, hydrolyzed animal protein and the like. Such conditioning agents may be present in an amount within the range of from about 0.01 to about 5% and preferably from about 0.05 to about 2% by weight and from about 0.1 to about 20% by weight depending upon the ultimate use of the skin preparation.

The process techniques will vary depending upon the particular ingredients present. In a preferred process, thickener such as stearic acid, emulsifier such as polysorbate 20 laurate (Tween 20) and glyceryl monostearate and sodium lauryl sulfate (Tegacid special), emollient, such as dimethicone (Silicon 225), preservative, such as propyl paraben, such screen agents (where present) and polyvinyl alkyl or alkenyl ester, such as polyvinyl stearate or polyvinyl oleate, are blended together with moderate mixing to form a first non-aqueous blend. A second blend of deionized water, gum thickener, such as Carbopol 940 and other water-soluble ingredients, if desired, and a third blend of humectant, for example, a polyethylene glycol (such as Carbowax 400) and preservative, such as methyl paraben and benzyl alcohol are formed. The first non-aqueous blend is sweep mixed into the second and third blends to form an emulsion. Thereafter, a blend of a small amount of deionized water and triethanolamine (neutralizer for Carbopol 940, if necessary) and other water-soluble ingredients which can be included with this aqueous phase is added to the emulsion with mixing. Thereafter, the final blend is cooled to room temperature, homogenized, stored or packaged.

Preferred sun block formulations offering maximum protection according to this invention include from about 60% to about 80% by weight of water, from about 1% to about 10% by weight of a polyvinyl alkyl or alkenyl ester such as polyvinyl stearate, from about 2.5% to about 3.5% by weight of UV-A absorbing agents selected from 2-hydroxy-4-methoxybenzophenone (oxybenzone) and 2,2'-dihydroxy-4-methoxybenzophenone (dioxybenzone), from about 5% to about 10% by weight of the UV-B absorbing agent 4-(dimethylamino)benzoic acid, 2-ethylhexyl ester (Escalol 507), from about 1 to about 5% by weight of humectants, from about 1% to about 5% by weight of emollients, from about 1% to about 5% by weight of emulsifiers, from about 0.1 to about 0.5% by weight thickeners, and up to about 1% by weight of combined preservatives, antioxidants, and fragrances.

Most preferably the maximum protection formulation will contain about 73% by weight of deionized water, about 5% by weight of polyvinyl stearate, about 3% by weight of 2-hydroxy-4-methoxybenzophenone up to about 1% by weight of 2,2'-dihydroxy-4-methoxybenzophenone, about 8% by weight of 4-(dimethylamino)benzoic acid, 2-ethylhexyl ester, about 3% by weight of emollients, about 5% by weight of emulsifiers, about 0.35% by weight thickener, and up to 1% by weight of combined preservatives, antioxidants, and fragrances.

Preferred sunscreen formulations which protect but still permit gradual tanning according to this invention contain from about 55% to about 65% by weight of water, from about 1 to about 10% by weight of polyvinyl alkyl or alkenyl ester, up to about 1% by weight of 2-hydroxy-4-methoxybenzophenone (oxybenzone), from about 3% to about 5% by weight of 4-(dimethylamino)benzoic acid, 2-ethylhexylester (Escalol 507), up to about 7.5% by weight of humectants, from about 1 to about 5% by weight of emollients, from about 1% to about 10% by weight of emulsifiers, and up to about 1% by weight of combined preservatives, antioxidants, and fragrances.

The most preferred sunscreen formulation which still permits tanning is a lotion containing from about 60% to about 61% by weight of deionized water, about 5% by weight of a polyvinyl stearate ester, about 0.6% by weight of 2-hydroxy-4-methoxybenzophenone, about 3.5% by weight of 4-(dimethylamino)benzoic acid, 2-ethylhexyl ester, about 5% by weight of glycerin or propylene glycol, about 2% to about 4% by weight of emollients, from about 3% to about 8% by weight of emulsifiers, and up to about 1% by weight of combined preservatives, antioxidants and fragrances.

Preferred moisturizer compositions will be similar to the sunscreen and sun block formulations set out above without the sunscreen agents.

The following Examples represent preferred embodiments of the invention. Unless otherwise indicated, all temperatures are expressed in degrees Centigrade.

EXAMPLE 1

A water-resistant sun block formulation (in the form of a oil-in-water type emulsion in thick lotion form) in accordance with the present invention having a sun protection factor (SPF) value of 15 having the following composition was prepared as described below.

The SPF value is determined by dividing minimal erythema dose (MED) for protected skin after the application of 2 mg/cm$^2$ of the formulation of the MED for unprotected skin.

| Ingredient | Parts by Weight |
|---|---|
| Blend I | |
| Glyceryl monostearate and Sodium lauryl sulfate (Tegacid special) (thickener and auxiliary emulsifier) | 2 |
| Stearic acid (thickener and emollient) | 3 |
| 2-Hydroxy-4-methylbenzophenone (UVinul M40 - sunscreen) | 3 |
| 4-(Dimethylamino)benzoic acid, 2-ethylhexyl ester (Escalol 507 - sunscreen) | 8 |
| Dimethicone (Silicone 225 - emollient) | 0.5 |
| Polysorbate 20 laurate (Tween 20 - emulsifier) | 1 |
| Propylparaben (Tegosept P - preservative) | 0.1 |
| Polyvinyl stearate | 5 |
| Blend II | |
| Deionized water | 71.2 |
| Acrylate polymer (Carbopol 940 - gum thickener) | 0.35 |
| Blend III | |
| Polyethylene glycol 400 (Carbowax 400 - humectant) | 2 |
| Methylparaben (Tegosept M - Preservative) | 0.2 |
| Benzyl alcohol (Preservative) | |
| Blend IV | |
| Deionized water | 2 |
| Triethanolamine | 1.2 |

Aqueous Blend II was prepared by dispersing the acrylate polymer in the deionized water. Blend III (prepared by simple mixing of ingredients) was then mixed with Blend II. The combined Blend II-III was then heated to 75° C.

Blend I was formed by simple mixing of the ingredients in a separate vessel while heating to 75° C.

Blend I (heated at 75° C.) was then added to the combined Blend II-III (also at 75° C.) with sweep mixing.

The combined Blend I-II-III was heated at 75° C. for 30 minutes, allowed to air cool to 60° C., and then Blend IV (prepared by simple mixing of ingredients) was added with sweep mixing. The resulting batch was then allowed to air cool to 30° C. to form the sun block formulation of the invention.

As a control, a formulation as described above without the polyvinyl stearate was prepared.

The Example I formulation was tested vis-a-vis the control formulation for wash resistancy using an in vitro testing method.

The in vitro testing method employed encompassed application of product (Example 1 or control) to a collagen substrate at a concentration of 2 ml/cm$^2$. This was allowed to dry at ambient temperature for 15 minutes and then was submerged in a water batch (25±3° C.) agitated by a homomixer for 40 minutes. These substrate/products were removed from the water and allowed to air dry for 15 minutes. They were then extracted with methanol and analyzed by HPLC for % sunscreens and subsequent relative sun protecting factors (SPF's). The results obtained are set out in Table A below.

TABLE A

| | After 40 Minute Wash | | |
|---|---|---|---|
| | | SPF | % SPF Retention After 40 minutes washing |
| Ex. 1 Formulation (with polyvinyl stearate) | Before wash After wash | 17.6 15.3 | 87% |
| Control (without polyvinyl stearate) | Before wash After wash | 17.7 3.63 | about 20% |

The above results clearly show that the Example 1 formulation of the invention which contained polyvinyl stearate had excellent wash resistance (87% SPF retention) even after 40 minutes of washing. The control formulation which did not contain polyvinyl stearate had relatively poor wash resistance (20% SPF retention after 40 minutes of washing).

EXAMPLE 2

A sun screen formulation in accordance with the present invention having the following composition and having a sun protection factor (SPF) value of 8 was prepared as described below.

The ingredients are listed on a parts by weight basis and the chemical, CTFA, and/or trade name are included. This formulation is an oil-in-water type emulsion in a thick lotion form.

| Ingredient | Parts by Weight |
|---|---|
| Blend IA | |
| Deionized water | 69.2 |
| Acrylate polymer (Carbopol 940- | 0.35 |

| Ingredient | Parts by Weight |
| --- | --- |
| gum thickener) | |
| Blend IB | |
| Glycerine (humectant) | 1 |
| Deionized water | 0.1 |
| Methylparaben (Tegosept M, preservative) | 0.25 |
| Blend II | |
| Cetyl alcohol (thickener emollient | 5 |
| Polysorbate 60 (Tween 60, emulsifier) | 2 |
| Glyceryl monostearate (Tegin, thickener) | 2 |
| Cetyl palmitate (Kessco X653, emollient) | 1 |
| Dimethicone (Silicone 200 (350 c.s.) emollient) | 1 |
| Petrolatum (emollient) | 0.5 |
| Propylparaben (Tegosept P, preservative) | 0.1 |
| 4-(Dimethylamino)benzoic acid, 2-ethylhexyl ester (Escalol 507, sun screen) | 4.25 |
| 2-Hydroxy-4-methoxybenzophenone/ 2,2'-dihydroxy-4-methoxy-benzo-phenone (Uvinul M-40/Spectra-Sorb UV-9) | 1.2 |
| Polyvinyl stearate | 5 |
| Blend III | |
| Deionized water | 2 |
| Sodium hydroxide | 0.16 |
| Perfume oil | 0.45 |
| Blend IV | |
| Deionized water | 2 |
| Potassium sorbate (Sorbistat-K, preservative) | 0.2 |
| Imidazolidinyl urea (Germall 115, preservative) | 0.45 |

Aqueous Blend IA was prepared by dispersing the acrylate polymer in the deionized water. Blend IB (prepared by simple mixing of ingredients) was then mixed with Blend IA. The combined Blend IA-B was then heated to 75° C.

Blend II was formed by simple mixing of the ingredients in a separate vessel while heating at 75° C.

Blend II (heated at 75° C.) was then added to the combined Blend IA-B (also at 75° C.) with sweep mixing.

The combined Blend IA-B-II was heated at 75° C. for 30 minutes, allowed to air cool to 60° C. and then Blends III and IV (each prepared by simple mixing) together with the perfume oil were added with sweep mixing.

The resulting batch was then allowed to air cool to 30° C. to form the sun screen formulation of the invention.

EXAMPLE 3

A sunscreen formulation having a sun protection factor value of 4 having the following composition was prepared as described below. The ingredients are listed on a parts by weight basis and both the CFTA and trade name are included. This formulation is an oil-in-water type emulsion having a motion consistency.

| Ingredient | Parts by Weight |
| --- | --- |
| Blend IA | |
| Deionized water | 72.5 |
| Acrylate polymer (Carbopol 940- | 0.25 |

| Ingredient | Parts by Weight |
| --- | --- |
| gum thickener) | |
| Blend IB | |
| Propylene glycol (humectant) | 3 |
| Methylparaben (Tegosept M, preservative) | 0.2 |
| Blend II | |
| Polyethylene glycol 23 - lauryl ether (Brij 35, Laureth 23, auxiliary emulsifier) | 2 |
| Sorbitan stearate (Arlacel 60, emulsifier) | 1 |
| 4-(Dimethylamino)benzoic acid, 2-ethylhexyl ester (Escalol 507, sun screen, UV-B) | 3.2 |
| $C_{12}$-$C_{15}$ alcohol benzoate (Finsolv TN, emollient) | 3 |
| Dimethicone (Silicone 225, emollient) | 1 |
| Propylparaben (Tegosept P, preservative) | 0.1 |
| Cetyl alcohol (thickener, emollient) | 2.5 |
| Polyvinyl stearate | 5 |
| Blend III | |
| Deionized water | 1 |
| Triethanolamine | 0.25 |
| Dimethyldimethoyl hydantoin (Glydant, preservative) | 0.2 |

Aqueous Blend IA was prepared by dispersing the acrylate polymer in the deionized water. Blend IB (prepared by simple mixing of ingredients) was then mixed with Blend IA. The combined Blend IA-B was then heated to 75° C.

Blend II was formed by simple mixing of the ingredients in a separate vessel while heating at 75° C.

Blend II (heated at 75° C.) was then added to the combined Blend IA-B (also at 75° C.) with sweep mixing.

The combined Blend IA-B-II was heated at 75° C. for 30 minutes, allowed to air cool to 60° C. and then Blend III (Prepared by simple mixing) was added with sweep mixing.

The resulting batch was then allowed to air cool to 30° C. to form the sun screen formulation of the invention.

EXAMPLE 4

A moisturizer formulation having the following composition was prepared as described below. The ingredients are listed on parts by weight basis and both the CTFA and trade name are included. The formulation is an oil-in-water type emulsion and is in the form of a lotion.

| Ingredient | Parts by Weight |
| --- | --- |
| Blend I | |
| Deionized water | 74.3 |
| Magnesium aluminum silicate (Veegum R, thickener) | 0.2 |
| dl-Panthenol (skin conditioner) | 0.5 |
| Allantoin (skin conditioner) | 0.2 |
| Blend II | |
| Polyethylene glycol (Carbowax 400, humectant) | 2 |
| Xanthan gum (Keltrol F, thickener) | 0.2 |
| Methylparaben (Tegosept M, preservative) | 0.2 |
| Blend III | |

| Ingredient | Parts by Weight |
|---|---|
| Isopropyl palmitate (emollient) | 2.5 |
| Cetearyl octanoate (Purcellin oil, emollient) | 4 |
| Propylene glycol dicaprate/dicaprylate (Standamul 302 emollient) | 8 |
| Propylparaben (Tegosept P, preservative) | 0.1 |
| Stearic acid (thickener) | 2 |
| Cetyl alcohol | 0.5 |
| Polyethylene glycol 100 stearate and glycerol monostearate (1:1) (Arlacel 165, emulsifier) | 2 |
| Polyethylene glycol 20 stearyl ether (Brij 78, emulsifier) | 2 |
| Polyvinyl stearate | 1 |
| Component IV | |
| Dimethyldimethoyl hydantoin (Glydant, preservative) | 0.3 |

Aqueous Blend IA was prepared by mixing the ingredients in the deionized water. Blend II (prepared by simple mixing of ingredients) was then mixed with Blend I. The combined Blends I-II was then heated to 75° C.

Blend III was formed by simple mixing of the ingredients in a separate vessel while heating at 75° C.

Blend III (heated at 75° C.) was then added to the combined Blend I-II-III (also at 75° C.) with sweep mixing.

The combined Blend I-II-III was heated at 75° C. for 30 minutes, allowed to air cool to 60° C. and then component IV was added with sweep mixing.

The resulting batch was then allowed to air cool to 30° C. to form the moisturizer formulation of the invention.

What is claimed is:

1. A moisture-resistant skin treatment composition in the form of a sunscreen composition or moisturizer composition, in the form of an oil-in-water emulsion or a water-in-oil emulsion, consisting essentially of from about 50 to about 90% by weight water, from about 1 to about 10% by weight emollient, from about 1 to about 10% by weight emulsifier, a preservative and a polyvinyl alkyl or alkenyl ester which is polyvinyl stearate, polyvinyl caprylate, polyvinyl pelargonate, polyvinyl caprate, polyvinyl undecanoate, polyvinyl laurate, polyvinyl tridecanoate, polyvinyl myristate, polyvinyl pentadecanoate, polyvinyl palmitate, polyvinyl margarate, polyvinyl monodecanoate, polyvinyl archidate, polyvinyl heneicosanoate, polyvinyl behenate, polyvinyl tricosanoate, polyvinyl tetracosanoate, polyvinyl pentacosanoate, polyvinyl oleate, polyvinyl linoleate, polyvinyl ricinoleate, polyvinyl palmitoleate, polyvinyl vaccenoate, polyvinyl erucoate, or polyvinyl licanoate in an amount within the range of from about 0.5 to about 10% by weight based on the total composition to impart moisture-resistance to said composition.

2. The composition as defined in claim 1 wherein said polyvinyl alkyl or alkenyl ester contains from about 12 to about 22 carbons in the alkyl or alkenyl portion.

3. The composition as defined in claim 1 wherein the polyvinyl alkyl or alkenyl ester is polyvinyl stearate, polyvinyl laurate, polyvinyl myristate, polyvinyl palmitate or polyvinyl oleate.

4. The composition as defined in claim 1 in the form of a moisture-resistant sun screen composition and includes from about 1 to about 15% by weight of at least one ultraviolet absorbing agent.

5. The composition as defined in claim 1 wherein the ultraviolet absorbing agents include one or more UV-A absorbing and one or more UV-B absorbing agents.

6. The composition as defined in claim 5 wherein the UV-A absorbing agent or agents are present at from about 0.5% to about 10% by weight and the UV-B absorbing agent or agents are present at from about 3% to about 10% by weight.

7. The composition as defined in claim 6 wherein the UV-A absorbing agent is one or more selected from the group consisting of 2-(2'-hydroxy-5'-methylphenyl)benzotriazole; 2-(2'-hydroxy-5'-t-octylphenyl)benzotriazole; 2,4-dihydroxybenzophenone; 2-hydroxy-4-methoxybenzophenone; 2,2', 4,4'-tetrahydroxybenzophenone; 2,2'-dihydroxy-4,4'-dimethoxybenzophenone; 2,2'-dihydroxy-4-methoxybenzophenone; 2-ethylhexyl-4-phenylbenzophenone carbonate; 2-hydroxy-4-methoxy-4'-methylbenzophenone; 2-hydroxy-4-(n-octyloxy)benzophenone; 4-phenylbenzophenone; and 2-ethylhexyl-2-cyano-3,3'-diphenylacrylate and the UV-B absorbing agent is one or more selected from the group consisting of 4-(dimethylamino)benzoic acid, ethyl ester; 4-(dimethylamino)benzoic acid, 2-ethylhexyl ester; 4-(dimethylamino)benzoic acid, pentyl ester; glyceryl p-aminobenzoate; isobutyl p-aminobenzoate; and isopropyl p-aminobenzoate.

8. The composition as defined in claim 6 wherein the UV-A absorbing agent is 2-hydroxy-4-methoxybenzophenone alone or in combination with 2,2'-dihydroxy-4-methoxybenzophenone and the UV-B absorbing agent is 4-(dimethylamino)benzoic acid, 2-ethylhexyl ester.

9. The composition as defined in claim 4 wherein the polyvinyl alkyl ester contains from 8 to 25 carbons in the alkyl portion.

10. The composition as defined in claim 9 wherein the polyvinyl alkyl ester is polyvinyl stearate.

11. The composition as defined in claim 1 wherein water is present in an amount of from about 50 to about 90% by weight, emollients are present in an amount of from about 1 to about 5% by weight, emulsifiers are present in an amount of from about 1 to about 10% by weight, thickeners are present in an amount of from about 0.1 to about 1% by weight, humectants are present in an amount of from about 1 to about 5% by weight, preservatives are present in an amount of from about 0.5 to about 1% by weight.

12. The composition as defined in claim 4 offering maximum ultraviolet protection and moisture resistance comprising from about 60% to about 80% by weight of water, from about 2% to about 7% by weight of polyvinyl alkyl or alkenyl ester, from about 1% to about 5% by weight of 2-hydroxy-4-methoxybenzophenone alone or in combination with 2,2'-dihydroxy-4-methoxybenzophenone, from about 5% to about 10% by weight of 4-(dimethylamino)benzoic acid, 2-ethylhexyl ester, from about 1% to about 5% by weight of emollients, from about 1% to about 10% by weight of emulsifiers, and up to about 1% by weight of combined preservatives, antioxidants and fragrances.

13. The composition of claim 12 comprising about 73% by weight of deionized water, about 5% by weight of polyvinyl stearate having an average molecular weight of about 10,000, about 2% to about 4% by weight of 2-hydroxy-4-methoxy-benzophenone, up to about 1% by weight of 2,2'-dihydroxy-4-methoxybenzophenone, about 8% by weight of 4-(dimethylamino)-benzoic acid, 2-ethylhexyl ester, from about 2% to about 4% by weight of emollients, from about 3% to about 8% by weight of emulsifiers, and up to about 1% by weight of combined preservatives, antioxidants and fragrances.

14. The method of enhancing the moisture resistant properties of a sun screen composition which contains one or more ultraviolet absorbing agents which comprises including at least about 0.5 by weight of a polyvinyl alkyl or alkenyl ester within the composition.

15. The method as defined in claim 14 wherein the sun screen composition contains from about 3% to about 15% by weight of ultraviolet absorbing agents and the polyvinyl alkyl or alkenyl ester is included at from about 0.5 to about 10% by weight of the composition.

16. The method as defined in claim 14 wherein the polyvinyl alkyl or alkenyl ester is polyvinyl stearate, polyvinyl laurate, polyvinyl myristate, polyvinyl palmitate, or polyvinyl oleate.

17. The method as defined in claim 16 wherein the polyvinyl alkyl ester is polyvinyl stearate.

18. The composition as defined in claim 1 further including a thickener in an amount within the range of from about 0.05 to about 1% by weight.

* * * * *

UNITED STATES PATENT AND TRADEMARK OFFICE
CERTIFICATE OF CORRECTION

PATENT NO. : 4,597,963

DATED : July 1, 1986

INVENTOR(S) : George E. Deckner

It is certified that error appears in the above-identified patent and that said Letters Patent is hereby corrected as shown below:

Column 2, line 46, "form" should read --from--.
Column 4, line 19, "such" , second occurrence, read -- sun --..
Column 5, line 34, "of" third occurrence should read --by--.

Signed and Sealed this

Twenty-eighth Day of October, 1986

[SEAL]

Attest:

DONALD J. QUIGG

Attesting Officer     Commissioner of Patents and Trademarks